United States Patent [19]

White

[11] Patent Number: 4,870,041
[45] Date of Patent: Sep. 26, 1989

[54] PROCESS FOR THE OLIGOMERIZATION OF ALPHA OLEFINS AND CATALYST THEREFOR

[75] Inventor: Mary A. White, El Cerrito, Calif.

[73] Assignee: Chevron Research Company, San Francisco, Calif.

[21] Appl. No.: 102,178

[22] Filed: Sep. 29, 1987

Related U.S. Application Data

[60] Continuation of Ser. No. 814,441, Dec. 30, 1985, abandoned, which is a division of Ser. No. 570,716, Jan. 13, 1984, Pat. No. 4,579,991.

[51] Int. Cl.$^4$ ............................................. C08F 4/64
[52] U.S. Cl. ..................................... 502/113; 585/524
[58] Field of Search ......................................... 502/113

[56] References Cited

U.S. PATENT DOCUMENTS

| | | | |
|---|---|---|---|
| 3,288,769 | 11/1966 | Cooper et al. | 502/113 X |
| 3,637,897 | 1/1972 | Cull et al. | 502/113 X |
| 3,812,089 | 5/1974 | Tashiro et al. | 502/113 X |
| 3,862,257 | 1/1975 | Buben et al. | 585/523 |
| 4,154,701 | 5/1979 | Melquist | 502/113 |
| 4,192,772 | 3/1980 | Berger et al. | 502/113 X |
| 4,396,788 | 8/1983 | Langer | 585/524 X |
| 4,409,414 | 10/1983 | Langer | 585/524 |

FOREIGN PATENT DOCUMENTS 1556506 11/1979 United Kingdom .

*Primary Examiner*—Patrick P. Garvin
*Attorney, Agent, or Firm*—C. J. Caroli; R. C. Gaffney

[57] ABSTRACT

A process for the preparation of alpha olefin oligomers having predominantly terminal unsaturation using a catalyst system comprising an alkyl aluminum halide component and a second component comprising at least one zirconium compound, preferably in combination with at least one titanium compound. There is also disclosed a catalyst composition for use in this process.

10 Claims, No Drawings

PROCESS FOR THE OLIGOMERIZATION OF ALPHA OLEFINS AND CATALYST THEREFOR

This is a continuation of application Ser. No. 814,441, filed Dec. 30, 1985 and now abandoned, which is a division of Ser. No. 570,716, filed Jan. 13, 1984 and now Patent No. 4,579,991.

BACKGROUND OF THE INVENTION

The present invention relates to a process for the oligomerization of alpha olefins. More specifically, the present invention relates to the preparation of alpha olefin oligomers having predominantly terminal unsaturation using a catalyst system comprising an alkyl aluminum halide component and a second component comprising at least one zirconium compound, preferably in combination with at least one titanium compound.

It is known in the art that alpha olefins are typically oligomerized using an acidic catalyst, normally either a Bronsted or Lewis acid. The oligomeric products derived from such acid-catalyzed oligomerization have mostly internal double bonds. These products also have a highly branched structure, due to isomerization side reactions.

In the presence of transition metal catalysts of the Ziegler-Natta type, alpha olefins generally polymerize to high molecular weight solid materials which are highly stereoregular. The preparation of a low molecular weight atactic polypropylene has been reported in the literature, however, employing a transition metal complex as a catalyst.

Hence, British Patent No. 1,231,299 describes a process for preparing a low molecular weight atactic polypropylene using a catalyst system containing an alkoxy titanium trichloride and a dialkyl aluminum chloride. This process provides a highly regular oligomeric product resulting from mostly head-to-tail addition of monomer units. However, as in acid-catalyzed oligomerization, the double bond in this material is also internal.

Belgian Patent No. 756,033 describes a process for converting ethylene to a mixture of linear alpha olefins having 4 to 40 carbon atoms, using a transition metal catalyst. The reaction product also contains high molecular weight solid polyethylene. The catalyst employed in this process comprises an alkyl aluminum halide and a zirconium complex, such as zirconium alkoxide, alkoxy zirconium halide, zirconium alkylamine and alkylamino zirconium halide.

SUMMARY OF THE INVENTION

The present invention provides a process for the preparation of low molecular weight alpha olefin oligomers having predominantly terminal unsaturation which comprises oligomerizing an alpha olefin having from 3 to 20 carbon atoms in the presence of a catalyst comprising (A) an alkyl aluminum halide component and (B) a catalyst component comprising at least one zirconium compound of the formula $$Zr(OR)_nX_{4-n}$$

wherein R is alkyl of 1 to 12 carbon atoms, aryl of 6 to 12 carbon atoms, or trialkyl silyl, wherein each alkyl has 1 to 6 carbon atoms; X is halogen; and n is an integer from 0 to 4.

In a preferred embodiment, component (B) of the catalyst additionally comprises at least one titanium compound of the formula $$Ti(OR')_mY_{4-m}$$

wherein R' is alkyl of 1 to 12 carbon atoms, aryl of 6 to 12 carbon atoms, or trialkyl silyl, wherein each alkyl has 1 to 6 carbon atoms; Y is halogen; and m is an integer from 0 to 4.

The present invention is further concerned with a catalyst composition for the oligomerization of alpha olefins which comprises (A) an alkyl aluminum halide component and (B) a catalyst component comprising at least one zirconium compound of the formula $$Zr(OR)_nX_{4-n}$$

in combination with at least one titanium compound of the formula $$Ti(OR')_mY_{4-m}$$

wherein R, R', X, Y, m and n are as described above.

Among other factors, the present invention is based on my discovery that alpha olefins containing three or more carbon atoms can be successfully oligomerized to provide low molecular weight oligomers having predominantly terminal unsaturation and a regular polymer backbone resulting from heat-to-tail addition of monomer units (that is, no isomerization has occurred), using a catalyst system containing an alkyl aluminum halide and at least one zirconium complex, preferably in combination with at least one titanium complex.

Advantageously, the oligomers prepared by the instant process are more reactive and yield products having better physical properties than do alpha olefin oligomers obtained by acid-catalyzed oligomerization processes.

Oligomers prepared by the process of the present invention are useful for a variety of applications, such as intermediates for the manufacture of detergents, paper sizing agents, and lubricating oil base stocks and additives.

DETAILED DESCRIPTION OF THE INVENTION

The catalyst composition used in the oligomerization process of the invention is a twocomponent system comprising (A) an alkyl aluminum halide component and (B) a second catalyst component comprising at least one zirconium compound, optionally in combination with at least one titanium compound.

The alkyl aluminum halides which are suitable for use in the catalyst system of the present process include dialkyl aluminum halides, alkyl aluminum dihalides, and alkyl aluminum sesquihalides having the empirical formula, $R_3''Al_2Z_3$, wherein R'' is alkyl and Z is halogen. In general, the alkyl group will contain from 1 to 20 carbon atoms, preferably from 1 to 6 carbon atoms.

Preferred alkyl aluminum halides are the alkyl aluminum sesquihalides, more preferably, the alkyl aluminum sesquichlorides. A particularly preferred alkyl aluminum halide is ethyl aluminum sesquichloride.

The second component of the oligomerization catalyst system comprises at least one tetravalent zirconium compound having the general formula

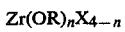

wherein R is alkyl of 1 to 12 carbon atoms, aryl of 6 to 12 carbon atoms, or trialkyl silyl, wherein each alkyl has 1 to 6 carbon atoms; X is halogen; and n is an integer from 0 to 4. Preferably, R is lower alkyl of 2 to 4 carbon atoms and X is chlorine. Suitable zirconium compounds encompassed by this formula include zirconium tetraalkoxides, $Zr(OR)_4$, alkoxy zirconium trihalides, $Zr(OR)X_3$, dialkoxy zirconium dihalides, $Zr(OR)_2X_2$, trialkoxy zirconium halides, $Zr(OR)_3X$, and zirconium tetrahalides, $ZrX_4$. Preferred zirconium catalyst components include zirconium tetra-n-propoxide, zirconium tetra-n-butoxide, di-n-butoxy zirconium dichloride, zirconium tetrachloride, and the mixture of zirconium tetra-n-propoxide and zirconium tetrachloride.

Although the oligomerization catalyst provides satisfactory results when component (B) comprises only zirconium compounds, I have found it preferable to employ the zirconium compound or compounds in combination with at least one tetravalent titanium compound. These titanium compounds have the general formula

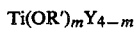

wherein R' is alkyl of 1 to 12 carbon atoms, aryl of 6 to 12 carbon atoms, or trialkyl silyl, wherein each alkyl has 1 to 6 carbon atoms; Y is halogen; and m is an integer from 0 to 4. Preferably, R' is lower alkyl of 2 to 4 carbon atoms and Y is chlorine. Suitable titanium compounds include titanium tetraalkoxides, $Ti(OR')_4$, alkoxy titanium trihalides, $Ti(OR')Y_3$, dialkoxy titanium dihalides, $Ti(OR')_2Y_2$, trialkoxy titanium halides, $Ti(OR')_3Y$, and titanium tetrahalides, $TiY_4$. Preferred titanium compounds include titanium tetra-n-propoxide, titanium tetra-n-butoxide, di-n-butoxy titanium dichloride, titanium tetrachloride.

A preferred catalyst system is obtained when component (B) comprises a zirconium tetrahalide and a titanium tetraalkoxide, such as the combination of zirconium tetrachloride and titanium tetra-n-butoxide. Another preferred catalyst system is obtained when component (B) comprises a zirconium tetraalkoxide and a titanium tetrahalide, such as the combination of titanium tetrachloride with zirconium tetra-n-propoxide or zirconium tetra-n-butoxide.

A particularly preferred catalyst system is obtained when component (B) comprises a zirconium tetraalkoxide, a titanium tetraalkoxide, and a titanium tetrahalide. Especially suitable is the combination of zirconium tetra-n-butoxide, titanium tetra-n-butoxide, and titanium tetrachloride.

When one or more zirconium compounds are combined with one or more titanium compounds, the mixture will generally have a zirconium to titanium molar ratio of 0.1:1 to 100:1, preferably about 0.3:1 to 3:1. Variation of the molar ratio of zirconium to titanium has been found to be effective in controlling the molecular weight of the oligomer produced.

The molar ratio of alkyl aluminum halide to transition metal or metals is important for optimum catalyst activity and for obtaining an oligomeric product having predominantly terminal unsaturation. Generally, the molar ratio of aluminum to zirconium or to zirconium plus titanium is from 12:1 to 3:1, preferably about 9:1 to 4:1.

In general, the alpha olefins suitable for use in the oligomerization process include olefins having from 3 to about 20 carbon atoms, preferably from 3 to about 10 carbon atoms, Typical olefins include propylene, 1-butene, 4-methyl-1-pentene, 1-hexene, 1-decene, and the like. The present process is particularly useful for the oligomerization of propylene.

The alpha olefins are oligomerized in contact with the present catalysts under conventional oligomerization conditions. Oligomerization is conducted at temperatures ranging from about 20° C. to 120° C., preferably from about 60° C. to 100° C. Oligomerization pressure is generally about 50 to 600 psig, preferably from about 150 to 500 psig. The reaction is normally carried out over a period of about 1 to 65 hours.

The oligomerization can be carried out either in the liquid or gaseous phase. When it is carried out in the liquid phase, an inert organic solvent can be used as a reaction medium or the olefin itself can be used as the reaction medium. Examples of inert organic solvents include aliphatic hydrocarbons of 3 to 8 carbon atoms, such as hexane or heptane; cycloaliphatic hydrocarbons, such as cyclohexane; and aromatics, such as benzene, toluene, xylene or chlorobenzene.

The regulation of the oligomer molecular weight during the oligomerization may be effected by changing the temperature of the oligomerization reaction. As mentioned above, the oligomer molecular weight may also be regulated by varying the molar ratio of zirconium to titanium in the catalyst.

The molecular weight range of the oligomers produced by the instant oligomerization process will generally correspond to about 2 to 30 monomer units of alpha olefin. For the oligomerization of propylene, the molecular weight of the oligomer formed with therefore fall into the range of about 84 to 1260.

The alpha olefin oligomers formed by the present process exhibit predominantly terminal unsaturation and a regular polymer backbone derived from head-to-tail addition of monomer units. Although the oligomeric product will normally contain some degree of internal unsaturation, the ration of alpha to internal double bond in the oligomer should exceed 50/50 and preferably will be at least 70/30.

The oligomerization can be carried out by any of batchwise, semi-continuous or continuous methods. It is also possible to perform the oligomerization in two or more stages under different reaction conditions.

The following examples are provided to illustrate the invention in accordance with the principles of the invention but are not to be construed as limiting the invention in any way except as indicated by the appended claims.

EXAMPLES

Abbreviations used in the following examples include "Me" for methyl, "Et" for ethyl, "Pr" for propyl, "iPr" for isopropyl and "Bu" for butyl.

EXAMPLE 1

Catalyst preparation: $Ti(Cl)_4$ (0.35 mmol), $Ti(OBu)_4$ (0.71 mmol) and $Zr(OBu)_4$ (0.35 mmol were mixed in a few ml of dry toluene and allowed to stir for 1 hour at room temperature under an inert atmosphere.

Propylene oligomerization: To a dry, nitrogen-purged, 1-liter autoclave were added the catalyst solution diluted with 50 ml of dry hexane, $Et_3Al_2Cl_3$ (4.4 mmol) and propylene (300 ml) which had been passed through a silica gel drying column. The autoclave was sealed and heated to 80° C. and the reaction mixture was stirred at 80° C. for 2 hours. The autoclave was then cooled, vented and the liquid product was washed with aqueous HCl to remove catalyst residue. 2.09 g solid polypropylene (PP) and 129.7 g liquid oligomer were recovered (86% propylene conversion). The number average molecular weight ($\overline{M}_n$) of the oligomeric product was 114 and 72% of the product had a terminal double bond (determined by $^{13}$C nmr spectroscopy).

EXAMPLE 2

Zr(OPr)$_4$ (1.06 mmol) was dissolved in 50 ml dry hexane and transferred to the autoclave. Et$_3$Al$_2$Cl$_3$ (4.4 mmol) was added. The propylene oligomerization was carried out as described in Example 1 except that the reaction was allowed to run for 17 hours. A trace of solid polypropylene was obtained along with liquid oligomer having 68% terminal double bond (approximately 90% propylene conversion).

EXAMPLES 3–12

These examples illustrate the effect of changing catalyst components and the Ti/Zr molar ratio. The catalysts were prepared as described in Example 1. Different amounts of various Ti and Zr complexes were used. The molar ratios of Ti/Zr are given in Table I and mmol Ti + mmol Zr always equaled 1.4 mmol. The propylene oligomerization reactions were carried out as in Example 1 except that the reactions were allowed to run for 17 hours. Percent regular, i.e., percent of oligomeric product having only head-to-tail addition of monomer units, was determined by infrared spectroscopy using oligomer having 100% regular structure as a reference [G. Natta, et al., J. Polymer Sci., A3, 1 (1965)]. The value obtained by this method was usually about 8% higher than the percent terminal double bond measured using $^{13}$C nmr spectroscopy.

Zr and 8.8 mmol Al were used in each of these examples. The results are shown in Table II.

TABLE II

| Example No. | Catalyst | % Regular | $M_n$ Oligomer | Amt Solid (g) | % C$_3$H$_6$ Conversion |
|---|---|---|---|---|---|
| 13 | Ti(OBu)$_4$/ZrCl$_4$/Et$_3$Al$_2$Cl$_3$ | 63 | 121 | 1.7 | 91 |
| 14 | Ti(OBu)$_4$/ZrCl$_4$/Me$_3$Al$_2$Cl$_3$ | 69 | 161 | 7.2 | 89 |
| 15 | Ti(OBu)$_4$/ZrCl$_4$/Et$_2$AlCl | 75 | 124 | 4.0 | 78 |
| 16 | Ti(OBu)$_4$/ZrCl$_4$/EtAlCl$_2$ | 59 | 158 | 0 | 25 |

EXAMPLE 17

TiCl$_4$ (0.17 mmol), Ti(OBu)$_4$ (0.35 mmol) and Zr(OBu)$_4$ (0.17 mmol) were mixed in a few ml toluene and allowed to stir for 1 hour at room temperature under an inert atmosphere. The solution was diluted with 50 ml dry hexane and transferred to the autoclave. Et$_3$Al$_2$Cl$_3$ (2.2 mmol) was added followed by 4-methyl-1-pentene (50 ml). The autoclave was sealed, the reaction mixture was heated to 80° C. and stirred for 65 hours. 87% of the monomer was converted to oligomeric product having $\overline{M}_n$ = 234.

EXAMPLE 18

The Ti/Zr catalyst was prepared as described in Example 1. The catalyst solution was added to a dry, nitrogen-purged, round-bottomed flask along with heptane (10 ml), Et$_3$Al$_2$Cl$_3$ (4.4 mmol) and 1-decene (100 ml). The solution was heated to 80° C. and stirred. The reaction was monitored by gas chromatography and after 4 hours, 86% conversion of 1-decene to oligomer having $\overline{M}_n$ = 356 had occurred.

What is claimed is:

1. A catalyst composition for the oligomerization of alpha olefins which consists essentially of (A) an alkyl aluminum halide component and (B) a second component consisting essentially of at least one zirconium compound of the formula $$Zr(OR)_nX_{4-n}$$

wherein R is alkyl of 1 to 12 carbon atoms, aryl of 6 to 12 carbon atoms, or trialkyl silyl, wherein each alkyl has 1 to 6 carbon atoms; X is halogen; and n is an integer from 0 to 4; in combination with at least one titanium compound of the formula $$Ti(OR')_mY_{4-m}$$

wherein R' is alkyl of 1 to 12 carbon atoms, aryl of 6 to 12 carbon atoms, or trialkyl silyl, wherein each alkyl has 1 to 6 carbon atoms; Y is halogen; and m is an integer

TABLE I

| Example No. | Catalyst | Ti/Zr Molar Ratio | % Regular | $M_n$ Oligomer | Amt Solid (g) | % C$_3$H$_6$ Conversion |
|---|---|---|---|---|---|---|
| 3 | Ti(OBu)$_4$/ZrCl$_4$/Et$_3$Al$_2$Cl$_3$ | 1/1 | 63 | 121 | 1.7 | 91 |
| 4 | Ti(OEt)$_4$/ZrCl$_4$/Et$_3$Al$_2$Cl$_3$ | 1/1 | 73 | 114 | 3.6 | 75 |
| 5 | Ti(OiPr)$_4$/ZrCl$_4$/Et$_3$Al$_2$Cl$_3$ | 1/1 | 59 | 168 | 1.0 | 59* |
| 6 | TiCl$_4$/Zr(OBu)$_4$/Et$_3$Al$_2$Cl$_3$ | 1/1 | 63 | 128 | 2.8 | 95 |
| 7 | TiCl$_4$/Zr(OPr)$_4$/Et$_3$Al$_2$Cl$_3$ | 1/1 | 62 | 121 | 2.9 | 91 |
| 8 | TiCl$_4$/Zr(OBu)$_4$/Et$_3$Al$_2$Cl$_3$ | 2/1 | 65 | 130 | 6.4 | 88 |
| 9 | TiCl$_4$/Zr(OBu)$_4$/Et$_3$Al$_2$Cl$_3$ | 3/1 | 70 | 148 | 11.0 | 77 |
| 10 | Ti(OBu)$_4$/ZrCl$_4$/Et$_3$Al$_2$Cl$_3$ | 3/1 | 79 | 125 | 1.7 | 86 |
| 11 | [TiCl$_4$ + 2Ti(OBu)$_4$]/Zr(OBu)$_4$/Et$_3$Al$_2$Cl$_3$ | 3/1 | 74 | 122 | 0.9 | 93 |
| 12 | [2TiCl$_4$ + Ti(OBu)$_4$]/Zr(OBu)$_4$/Et$_3$Al$_2$Cl$_3$ | 3/1 | 73 | 136 | 8.7 | 89 |

*After 6 hours.

EXAMPLES 13–16

These examples show that various alkyl aluminum co-catalysts may be used. Catalyst preparation and propylene oligomerization were carried out as described in Example 1 except that the reactions were allowed to run for 17 hours. 0.71 mmol Ti, 0.71 mmol from 0 to 4; with the proviso that at least one of the compounds of component (B) is a titanium tetraalkoxide.

2. The composition according to claim 1, wherein the alkyl aluminum halide is an alkyl aluminum sesquihalide.

3. The composition according to claim 2, wherein the alkyl aluminum sesquihalide is an alkyl aluminum sesquichloride.

4. The composition according to claim 3, wherein the alkyl aluminum sesquichloride is ethyl aluminum sesquichloride.

5. The composition according to claim 1, wherein component (B) consists essentially of a zirconium tetrahalide and a titanium tetraalkoxide.

6. The composition according to claim 5, wherein the component (B) consists essentially of zirconium tetrachloride and titanium tetra-n-butoxide.

7. The composition according to claim 1, wherein component (B) consists essentially of a zirconium tetraalkoxide, a titanium tetraalkoxide and a titanium tetrahalide.

8. The composition according to claim 7, wherein component (B) consists essentially of zirconium tetra-n-butoxide, titanium tetra-n-butoxide, and titanium tetrachloride.

9. The composition according to claim 1, wherein the aluminum to zirconium plus titanium molar ratio is from 12:1 to 3:1.

10. The composition according to claim 9, wherein the aluminum to zirconium plus titanium molar ratio is from 9:1 to 4:1.

* * * * *